US00PP12312P2

(12) United States Plant Patent
Salmon

(10) Patent No.: US PP12,312 P2
(45) Date of Patent: Dec. 25, 2001

(54) BRACTEANTHA PLANT NAMED 'FLORABELLA WHITE'

(75) Inventor: Alexander David Salmon, Gapsted (AU)

(73) Assignee: Outback Plants Pty. Ltd., Victoria (AU)

( * ) Notice: Subject to any disclaimer, the term of this patent is extended or adjusted under 35 U.S.C. 154(b) by 19 days.

(21) Appl. No.: 09/740,535

(22) Filed: Dec. 20, 2000

(51) Int. Cl.[7] ..... A01H 5/00
(52) U.S. Cl. ..... Plt./359
(58) Field of Search ..... Plt./359

(56) References Cited

PUBLICATIONS

GTITM UPOV ROM Citation for 'Florabella White' as per CA PBR 99–2000; Dec. 20, 1999.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of *Bracteantha bracteata* named 'Florabella White', characterized by its upright, outwardly spreading and rounded plant form; compact plant habit; small lanceolate leaves; white-colored involucral bracts and yellow-colored disc florets; and short peduncles that hold inflorescences above the foliage.

1 Drawing Sheet

BACKGROUND OF THE INVENTION

The present invention relates to a new and distinct cultivar of Bracteantha plant, botanically known as *Bracteantha bracteata* and referred to by the cultivar name 'Florabella White'.

The new Bracteantha is a product of a planned breeding program conducted by the Inventor in Gapsted, Victoria, Australia. The objective of the program is to create and develop Bracteantha cultivars with a compact growth habit, small leaves, numerous inflorescences, bright involucral bract colors, and short peduncles.

The new Bracteantha originated from a cross by the Inventor of an unidentified yellow involucral bract-colored proprietary selection of *Bracteantha bracteata* as the female, or seed, parent with an unidentified white involucral bract-colored proprietary selection of *Bracteantha bracteata* as the male, or pollen, parent. The new Bracteantha was discovered and selected by the Inventor as a plant within the progeny of the stated cross in a controlled environment in Gapsted, Victoria, Australia in 1997. The selection of the new Bracteantha was based on its growth habit, leaf size and peduncle length as plants of the new Bracteantha are more compact, have smaller leaves and shorter peduncles than plants of the parent selections.

Asexual reproduction of the new Bracteantha by terminal cuttings taken in a controlled environment in Gapsted, Victoria, Australia, has shown that the unique features of this new Bracteantha are stable and reproduced true to type in successive generations.

The new Bracteantha has not been observed under all possible environmental conditions. The phenotype may vary somewhat with variations in environment such as temperature, daylength, light intensity, photoperiod, and water and nutritional status without, however, any variance in genotype.

The following characteristics have been repeatedly observed and are determined to be basic characteristics of 'Florabella White' and distinguish the new Bracteantha as a new and distinct cultivar:

1. Upright, outwardly spreading and rounded plant form.
2. Compact plant habit.
3. Small lanceolate leaves.
4. White-colored involucral bracts and yellow-colored disc florets.
5. Short peduncles that hold inflorescences above the foliage.

Plants of the new Bracteantha differ from its sibling cultivars, 'Florabella Gold', U.S. Plant patent application Ser. No. 09/740,532, and 'Florabella Pink', U.S. Plant patent application Ser. No. 09/740,534 primarily in involucral bract coloration.

The new Bracteantha can be compared to the *Bracteantha bracteata* cultivar 'Nullabor Spectrum', disclosed in U.S. Plant patent application Ser. No. 08/938,583 (abandoned). In side-by-side comparisons conducted by the Inventor in Gapsted, Victoria, Australia, plants of the new Bracteantha differ in involucral bract color and are more compact, have shorter and narrower leaves, and have slightly smaller inflorescences than plants of 'Nullabor Spectrum'.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Bracteantha. The photograph comprises a side perspective view of a typical plant of 'Florabella White' in a container.

DETAILED BOTANICAL DESCRIPTION

The following observations, measurements and values describe plants grown in Gapsted, Victoria, Australia, under outdoor conditions with day temperatures ranging from 15 to 40° C., night temperatures ranging from 8 to 25° C., and light levels ranging from 5,000 to 9,000 foot candles. Rooted liners of the new Bracteantha were planted in 15-cm containers and grown for about 8 to 10 weeks. Color references are made to The Royal Horticultural Society Colour Chart except where general terms of ordinary dictionary significance are used.

Classification:

*Botanical.*—*Bracteantha bracteata* cultivar 'Florabellla White'.

Parentage:

*Male or pollen parent.*—Unidentified white involucral bract-colored selection of *Bracteantha bracteata,* not patented.

*Female or seed parent.*—Unidentified yellow involucral bract-colored selection of *Bracteantha bracteata,* not patented.

Propagation:

*Type.*—By cuttings.

*Time to initiate roots.*—Summer: About 10 to 20 days at temperatures of 20 to 25° C. Winter: About 15 to 35 days at temperatures of 20° C.

*Root description.*—Fine to fibrous, freely branching.

Plant description:

*General appearance.*—Upright, outwardly spreading and rounded herbaceous plant with lanceolate foliage and inflorescences held above the foliage on short peduncles. Appropriate for 15 pots to 25-cm hanging basket containers.

*Crop time.*—Moderately fast growth rate; to produce a finished 15-cm containerized plant from rooted cuttings, about 8 to 10 weeks are required depending on temperature and light level.

*Plant height.*—About 30 to 45 cm from soil level to top of inflorescences.

*Plant width.*—About 35 to 45 cm.

*Branching.*—Moderate, removal of terminal apex enhances branching; typically about 5 to 12 lateral branches per plant.

*Lateral branch description.*—Length: About 9 to 26 cm. Width: About 4 to 6 mm. Internode length: About 0.8 to 2.5 cm. Texture: Slightly pubescent; sometimes with very faint ridges. Color: 143C.

*Foliage description.*—Arrangement: Alternate, single. Quantity: About 21 to more than 60 per lateral branch. Shape: Lanceolate. Margin: Entire; slightly recurved. Apex: Acute. Base: Decurrent, clasping. Length: About 2.9 to 11.8 cm. Width: About 0.4 to 1.8 cm. Texture: Thin; slightly rough; moderately pubescent on both surfaces. Color: Young leaves, upper surface: 147A. Young leaves, lower surface: 147B. Fully mature leaves, upper surface: 146A; venation, 144D. Fully mature leaves, lower surface: 146B; venation, 145B.

Flowering description:

*Inflorescence form.*—Daisy-type composite inflorescence form. Inflorescences arranged acropetally on a capitulum.

*Inflorescence longevity.*—Inflorescences last on the plant for 4 to 6 weeks and 2 to 3 weeks as a fresh cut flower, and more than 6 weeks as a dried cut flower. Inflorescences persistent.

*Natural flowering season.*—Natural flowering season is spring to fall. Plants flower continuously during this period. Inflorescences close when wet and open when dry.

*Quantity of inflorescences.*—About 1 to 3 inflorescences and about 2 to 4 flower buds per lateral branch.

*Inflorescence aspect.*—Flat to slightly cupped.

*Inflorescence diameter.*—About 4.2 to 5.1 cm.

*Inflorescence depth* (*height*).—About 1.6 to 2.2 cm.

*Disc diameter.*—About 1.2 to 2.2 cm.

*Fragrance.*—Slight honey.

*Involucral bracts.*—Appearance: Satiny. Texture: Papery. Aspect: Flat. Shape: Triangular. Margin: Entire. Apex: Acute. Base: Truncate. Length: About 0.9 to 1.8 cm. Width: About 2 to 6 mm. Color: When opening, upper surface: 156D to 155C. When opening, lower surface: 155A to 159C. Mature, upper surface: 155A to 155C; with development, to 158D. Mature, lower surface: 155A to 162D.

*Disc florets.*—Shape: Tubular with five lobes. Diameter: About 1 mm. Width: About 1 mm. Color: Immature: 145C. Mature: 25B.

*Peduncle.*—Length: About 12.5 to 18.2 cm. Aspect: Erect to about 25° from vertical. Strength: Moderately strong, brittle when young, inflorescences held erect above foliage. Color: 143C to 146D. Texture: Slightly rough and pubescent.

*Flower bud.*—Shape: Broadly ovoid. Length: About 1.2 to 1.6 cm. Diameter: About 1.2 to 1.7 cm. Color: 161A to 161D.

*Androecium.*—Only present on disc florets. Stamen number: One per disc floret. Anther shape: Linear. Anther color: 24B. Amount of pollen: Moderate. Pollen color: 23A.

*Gynoecium.*—Present on disc florets. Pistil number: One per disc floret. Style length: About 3 mm. Style color: 23C. Stigma shape: Bilobate. Stigma color: 23C.

*Seed.*—Seed production has been observed.

Disease resistance: Susceptible to White Rust, causal agent *Albugo candida.*

It is claimed:

1. A new and distinct cultivar of Bracteantha plant named 'Florabella White', as illustrated and described.

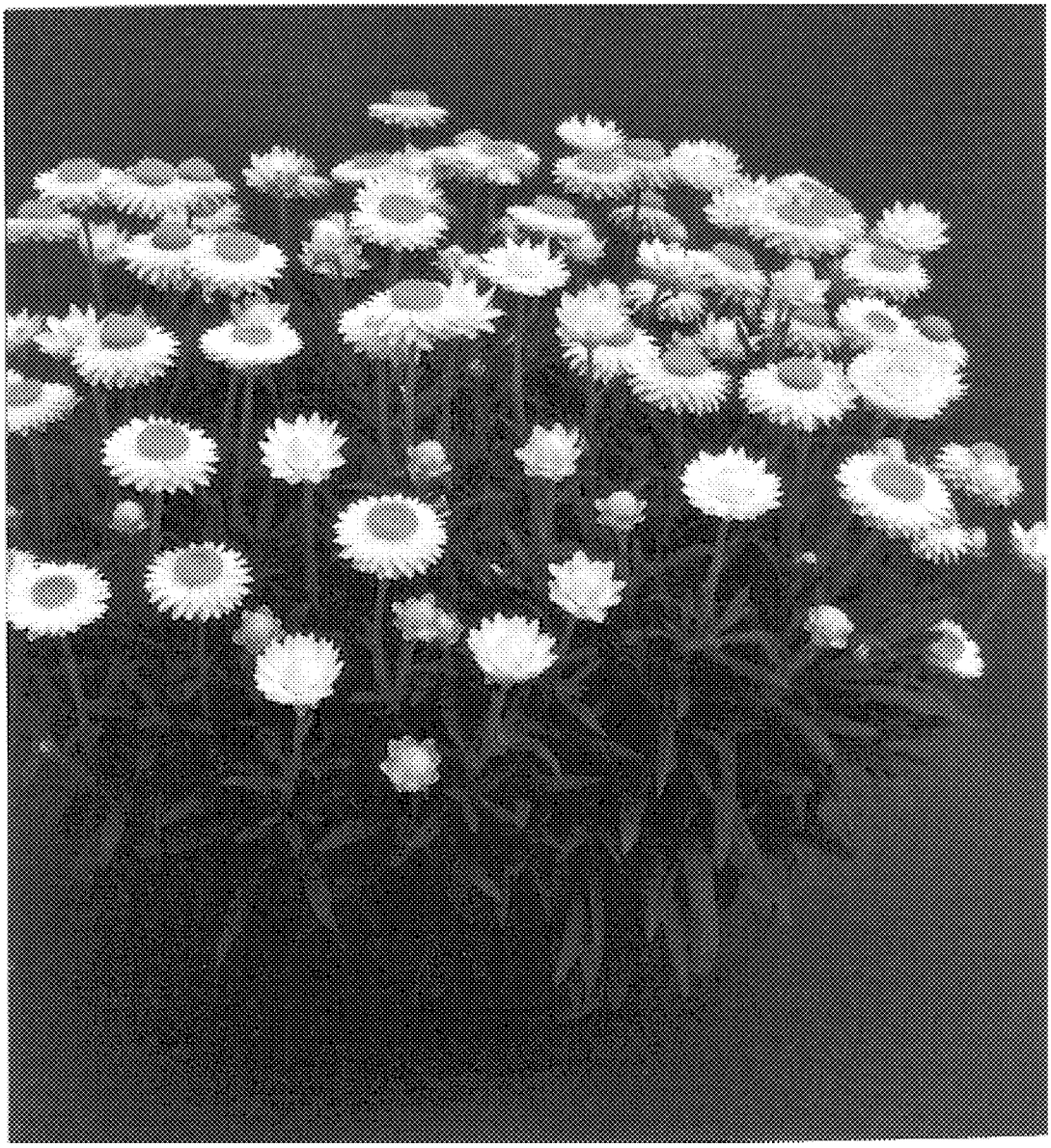

* * * * *